(12) United States Patent
Jaax et al.

(10) Patent No.: US 8,315,704 B2
(45) Date of Patent: Nov. 20, 2012

(54) STIMULATION OF A STIMULATION SITE WITHIN THE NECK OR HEAD

(75) Inventors: Kristen N. Jaax, Saugus, CA (US); Todd K. Whitehurst, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 12/940,862

(22) Filed: Nov. 5, 2010

(65) Prior Publication Data

US 2011/0060382 A1    Mar. 10, 2011

Related U.S. Application Data

(62) Division of application No. 11/259,176, filed on Oct. 25, 2005, now Pat. No. 7,853,321.

(60) Provisional application No. 60/661,700, filed on Mar. 14, 2005.

(51) Int. Cl.
*A61N 1/05* (2006.01)
(52) U.S. Cl. .......................................... 607/45; 607/116
(58) Field of Classification Search .................. 607/1, 2, 607/45, 46, 116, 117
See application file for complete search history.

(56) References Cited

U.S. PATENT DOCUMENTS

| 3,760,984 A | 9/1973 | Theeuwes |
| 3,845,770 A | 11/1974 | Theeuwes et al. |
| 3,916,899 A | 11/1975 | Theeuwes et al. |
| 3,923,426 A | 12/1975 | Theeuwes |
| 3,987,790 A | 10/1976 | Eckenhoff et al. |
| 3,995,631 A | 12/1976 | Higuchi et al. |

(Continued)

FOREIGN PATENT DOCUMENTS

WO    WO 01/82398 A1    1/2001

(Continued)

OTHER PUBLICATIONS

Office Communication for U.S. Appl. No. 12/188,781 mailed Jun. 10, 2011.

(Continued)

*Primary Examiner* — Scott Getzow
*Assistant Examiner* — Amanda Patton
(74) *Attorney, Agent, or Firm* — Frommer Lawrence & Haug LLP; Bruce E. Black

(57) ABSTRACT

Methods of applying a stimulus to a stimulation site within the neck or head of a patient include implanting a distal portion of one or more leads adjacent to the stimulation site, forming a loop with a proximal portion of the one or more leads, and securing the distal and proximal portions of the one or more leads to one or more securing sites with one or more securing devices. The distal portion of the one or more leads includes a number of electrodes disposed thereon that are configured to deliver the stimulus to the stimulation site. Systems for applying a stimulus to a stimulation site within the neck or head of a patient include one or more leads having a number of electrodes disposed on a distal portion thereof and one or more securing devices configured to secure the one or more leads to one or more securing sites. The distal portion of the one or more leads is implanted adjacent to the stimulation site and the electrodes are configured to deliver the stimulus to the stimulation site. The proximal portion of the one or more leads is formed in a loop.

16 Claims, 11 Drawing Sheets

U.S. PATENT DOCUMENTS

| | | | |
|---|---|---|---|
| 4,016,880 A | 4/1977 | Theeuwes et al. |
| 4,036,228 A | 7/1977 | Theeuwes |
| 4,111,202 A | 9/1978 | Theeuwes |
| 4,111,203 A | 9/1978 | Theeuwes |
| 4,203,440 A | 5/1980 | Theeuwes |
| 4,203,442 A | 5/1980 | Michaels |
| 4,210,139 A | 7/1980 | Higuchi |
| 4,327,725 A | 5/1982 | Cortese et al. |
| 4,360,019 A | 11/1982 | Portner et al. |
| 4,487,603 A | 12/1984 | Harris |
| 4,562,751 A | 1/1986 | Nason et al. |
| 4,627,850 A | 12/1986 | Deters et al. |
| 4,678,408 A | 7/1987 | Nason et al. |
| 4,685,903 A | 8/1987 | Cable et al. |
| 4,692,147 A | 9/1987 | Duggan |
| 4,725,852 A | 2/1988 | Gamblin et al. |
| 4,865,845 A | 9/1989 | Eckenhoff et al. |
| 4,867,164 A | 9/1989 | Zabara |
| 5,057,318 A | 10/1991 | Magruder et al. |
| 5,059,423 A | 10/1991 | Magruder et al. |
| 5,080,653 A | 1/1992 | Voss et al. |
| 5,097,122 A | 3/1992 | Colman et al. |
| 5,112,614 A | 5/1992 | Magruder et al. |
| 5,137,727 A | 8/1992 | Eckenhoff |
| 5,193,539 A | 3/1993 | Schulman et al. |
| 5,193,540 A | 3/1993 | Schulman et al. |
| 5,215,086 A | 6/1993 | Terry, Jr. et al. |
| 5,218,959 A | 6/1993 | Fenster |
| 5,234,692 A | 8/1993 | Magruder et al. |
| 5,234,693 A | 8/1993 | Magruder et al. |
| 5,273,053 A * | 12/1993 | Pohndorf | 607/132 |
| 5,312,439 A | 5/1994 | Loeb |
| 5,376,108 A | 12/1994 | Collins et al. |
| 5,400,784 A | 3/1995 | Durand et al. |
| 5,501,703 A | 3/1996 | Holsheimer et al. |
| 5,540,734 A | 7/1996 | Zabara |
| 5,584,874 A * | 12/1996 | Rugland et al. | 607/132 |
| 5,603,730 A * | 2/1997 | Romkee | 607/116 |
| 5,728,396 A | 3/1998 | Peery et al. |
| 5,938,688 A | 8/1999 | Schiff |
| 6,016,449 A | 1/2000 | Fischell et al. |
| 6,051,017 A | 4/2000 | Loeb et al. |
| 6,122,545 A | 9/2000 | Struble et al. |
| 6,161,044 A | 12/2000 | Silverstone |
| 6,164,284 A | 12/2000 | Schulman et al. |
| 6,185,452 B1 | 2/2001 | Schulman et al. |
| 6,208,894 B1 | 3/2001 | Schulman et al. |
| 6,219,580 B1 | 4/2001 | Faltys et al. |
| 6,272,382 B1 | 8/2001 | Faltys et al. |
| 6,280,873 B1 | 8/2001 | Tsukamoto |
| 6,308,101 B1 | 10/2001 | Faltys et al. |
| 6,368,315 B1 | 4/2002 | Gillis et al. |
| 6,381,496 B1 | 4/2002 | Meadows et al. |
| 6,393,325 B1 | 5/2002 | Mann et al. |
| 6,458,171 B1 | 10/2002 | Tsukamoto |
| 6,487,446 B1 | 11/2002 | Hill et al. |
| 6,505,075 B1 | 1/2003 | Weiner |
| 6,516,227 B1 | 2/2003 | Meadows et al. |
| 6,539,263 B1 | 3/2003 | Schiff et al. |
| 6,553,263 B1 | 4/2003 | Meadows et al. |
| 6,596,439 B1 | 7/2003 | Tsukamoto et al. |
| 6,605,382 B2 | 8/2003 | Ruth et al. |
| 6,605,383 B1 | 8/2003 | Wu |
| 6,620,151 B2 | 9/2003 | Blischak et al. |
| 6,666,845 B2 | 12/2003 | Hooper et al. |
| 6,735,475 B1 | 5/2004 | Whitehurst et al. |
| 6,740,072 B2 | 5/2004 | Starkweather et al. |
| 6,760,626 B1 | 7/2004 | Boveja |
| 6,770,067 B2 | 8/2004 | Lorenzen et al. |
| 7,082,337 B2 * | 7/2006 | Sommer et al. | 607/132 |
| 7,187,981 B2 | 3/2007 | Tanaka |
| 7,389,149 B2 | 6/2008 | Rossing et al. |
| 2001/0046625 A1 | 11/2001 | Ruth, II et al. |
| 2001/0053476 A1 | 12/2001 | Ruth et al. |
| 2002/0013612 A1 | 1/2002 | Whitehurst |
| 2005/0004637 A1 | 1/2005 | Singhal et al. |
| 2005/1000463 | 1/2005 | Singhal et al. |
| 2008/0132980 A1 | 6/2008 | Gerber |

FOREIGN PATENT DOCUMENTS

| | | |
|---|---|---|
| WO | WO 03/005465 A1 | 1/2003 |

OTHER PUBLICATIONS

Davis, R., "Notes Regarding Discussion with Dr. Giancarlo Barolat," Apr. 11, 2005.

Official Communication for U.S. Appl. No. 12/188,781, mailed Jul. 29, 2010.

Official Communication for U.S. Appl. No. 12/188,781, mailed Nov. 15, 2010.

Official Communication for U.S. Appl. No. 12/188,781, mailed Apr. 8, 2011.

Office Communication for U.S. Appl. No. 12/188,781 mailed Nov. 22, 2011.

Office Communication for U.S. Appl. No. 12/948,416 mailed Dec. 13, 2011.

U.S. Appl. No. 11/728,816, Office Communication mailed Jan. 22, 2010.

U.S. Appl. No. 12/188,781, Office Communication mailed Feb. 4, 2010.

U.S. Appl. No. 11/259,176, Office Communication mailed Jan. 30, 2008.

U.S. Appl. No. 11/259,176, Office Communication mailed Jun. 26, 2008.

U.S. Appl. No. 11/259,176, Office Communication mailed Nov. 18, 2008.

U.S. Appl. No. 111259,176, Office Communication mailed Apr. 29, 2009.

U.S. Appl. No. 11/259,176, Office Communication mailed Oct. 19, 2009.

U.S. Appl. No. 11/259,176, Office Communication mailed Mar. 29, 2010.

U.S. Appl. No. 11/256,356, Office Communication mailed May 15, 2009, 12 pages.

"Medtronic begins study of occipital nerve stimulation for chronic, refactory magraine headaches (Medtronic Inc.)(Brief Article)," Transplant News, Transplant Communications, Inc. 2004, HighBeam Reasearch, May 9, 2009, http://www.highbeam.com, 1 page.

"Headache Types," The Complete Guide to Headache, National Headache Foundation, May 9, 2009, http://headaches.org/educational_modules/completeguide/tension2a.html, 1 page.

Shellock, Frank G. et al., "Vagus Nerve Stimulation Therapy System: In Vitro Evaluation of Magnetic Resonance Imaging-Related Heating and Function at 1.5 and 3 Telsa," Cyberonics, Houston, TX, 2006.

"Physician's Manual," Sep. 2001, Cyberonics, Inc, Houston, TX.

* cited by examiner

STIMULATION OF A STIMULATION SITE WITHIN THE NECK OR HEAD

RELATED APPLICATIONS

This patent application is a divisional of U.S. patent application Ser. No. 11/259,176, filed Oct. 25, 2005, which claims the benefit of U.S. Provisional Patent Application Ser. No. 60/661,700, filed Mar. 14, 2005, both of which are hereby incorporated by reference in their entirety.

BACKGROUND

The public health significance of many medical, psychiatric, and neurological conditions and/or disorders is often overlooked, probably because of their episodic nature and the lack of mortality attributed to them. However, some medical conditions, such as headaches and facial pain, are often incapacitating, with considerable impact on social activities and work, and may lead to the significant consumption of drugs.

Migraine headaches are a particular form of headache, usually very intense and disabling. Migraines are a neurological disease thought to be of vascular origin. Migraines are characterized by attacks of sharp pain usually involving one half of the skull and accompanied by nausea, vomiting, phonophobia, photophobia and occasionally visual, olfactory or balance disturbances known as aura. The symptoms and their timing vary considerably among migraine sufferers and, to a lesser extent, from one migraine attack to the next. Migraine is often connected with the expansion of the blood vessels of the head and neck.

Migraine headaches can accompany, or be confused with, other types of headache, such as tension headaches. Since the treatment for other forms of headache may differ from that for migraine, it is important to recognize when migraine, tension or other forms of headache are occurring. In some cases, migraine headaches can cause seizures. Additionally, stroke symptoms (passing or permanent) are seen in very severe subtypes.

Migraine headaches often run in families and frequently start in adolescence, although some research indicates that it can start in early childhood or even in utero. Migraines occur more frequently in women than men, and are most common between ages 15-45, with the frequency of attacks declining with age in most cases. Because their symptoms vary, an intense headache may be misdiagnosed as a migraine by a layperson.

Conventional treatments for migraines focus on three areas: trigger avoidance, symptomatic control, and preventive drugs. Each of these will be discussed below.

In a minority of patients, the incidence of migraine can be reduced through diet changes to avoid certain chemicals that serve as a trigger for the migraine. These chemical triggers may be present in such foods as cheddar cheese and chocolate, and in most alcoholic beverages. Other triggers may be situational and can be avoided through lifestyle changes. Such triggers may include particular points in the menstrual cycle, certain weather patterns, or hunger. Bright flashing lights may also be a trigger. Most migraine sufferers are sensitive to and avoid bright or flickering lights.

If a migraine occurs despite trigger avoidance, the next step in treatment is symptomatic control. Caffeine and simple pain killers, analgesics, such as paracetamol, aspirin or low doses of codeine are sometimes, but not often, effective. Anti-emetics by suppository or injection may be needed in cases where vomiting dominates the symptoms. Generally, the earlier these drugs are taken in the attack, the better their effect. Narcotic pain medications, such as heroin, morphine, and other opiates, provide variable relief. However, their side effects and ability to cause serious drug addiction contraindicates their general use.

Sumatriptan (Imitrex®) and the related 5-hydroxytryptamine (serotonin) receptor agonists are now available and are the therapy of choice for severe migraine attacks. They are highly effective, reducing or abolishing all the symptoms within 30 to 90 minutes. These drugs have few side effects if used in correct dosage and frequency. However, about 20-30% of patients do not respond.

Evidence is accumulating that these drugs are effective because they constrict certain blood vessels in the brain. They do this by acting at serotonin receptors on nerve endings. This action leads to a decrease in the release of a peptide known as CGRP. In a migraine attack, this peptide is released and may produce pain by dilating cerebral blood vessels.

In addition to treating symptoms, preventive medication may also be administered on a daily basis if attacks occur more often than every two weeks. A large number of preventative medications with varying modes of action can be used. Selection of a suitable medication for any particular patient is a matter of trial and error, since the effectiveness of individual medications varies widely from one patient to the next. Beta blockers such as propranolol and atenolol are usually tried first. Antidepressants such as amitriptyline may be effective. Antispasmodic drugs are used less frequently. Sansert was effective in many cases, but has been withdrawn from the U.S. market.

Migraine sufferers also usually develop their own coping mechanisms for intractable pain. A cold or hot shower directed at the head, less often a warm bath, or resting in a dark and silent room may be as helpful as medication for many patients.

SUMMARY

Methods of applying a stimulus to a stimulation site within the neck or head of a patient include implanting a distal portion of one or more leads adjacent to the stimulation site, forming a loop with a proximal portion of the one or more leads, and securing the distal and proximal portions of the one or more leads to one or more securing sites with one or more securing devices. The distal portion of the one or more leads includes a number of electrodes disposed thereon that are configured to deliver the stimulus to the stimulation site.

Systems for applying a stimulus to a stimulation site within the neck or head of a patient include one or more leads having a number of electrodes disposed on a distal portion thereof and one or more securing devices configured to secure the one or more leads to one or more securing sites. The distal portion of the one or more leads is implanted adjacent to the stimulation site and the electrodes are configured to deliver the stimulus to the stimulation site. The proximal portion of the one or more leads is formed in a loop.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Methods and systems for applying a stimulus to a stimulation site within the neck or head of a patient are described herein. The methods and systems may be used to treat migraines or other medical conditions. One or more leads having a number of electrodes disposed on a distal portion thereof are implanted such that the distal portion is adjacent to one or more of the occipital nerves. Each lead includes a proximal portion that is formed in a loop. Suture sleeves secure the distal and proximal portions of the one or more leads to one or more securing sites (e.g., fascia). The loop and the suture sleeves are configured to minimize migration or slippage of the leads.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1A:
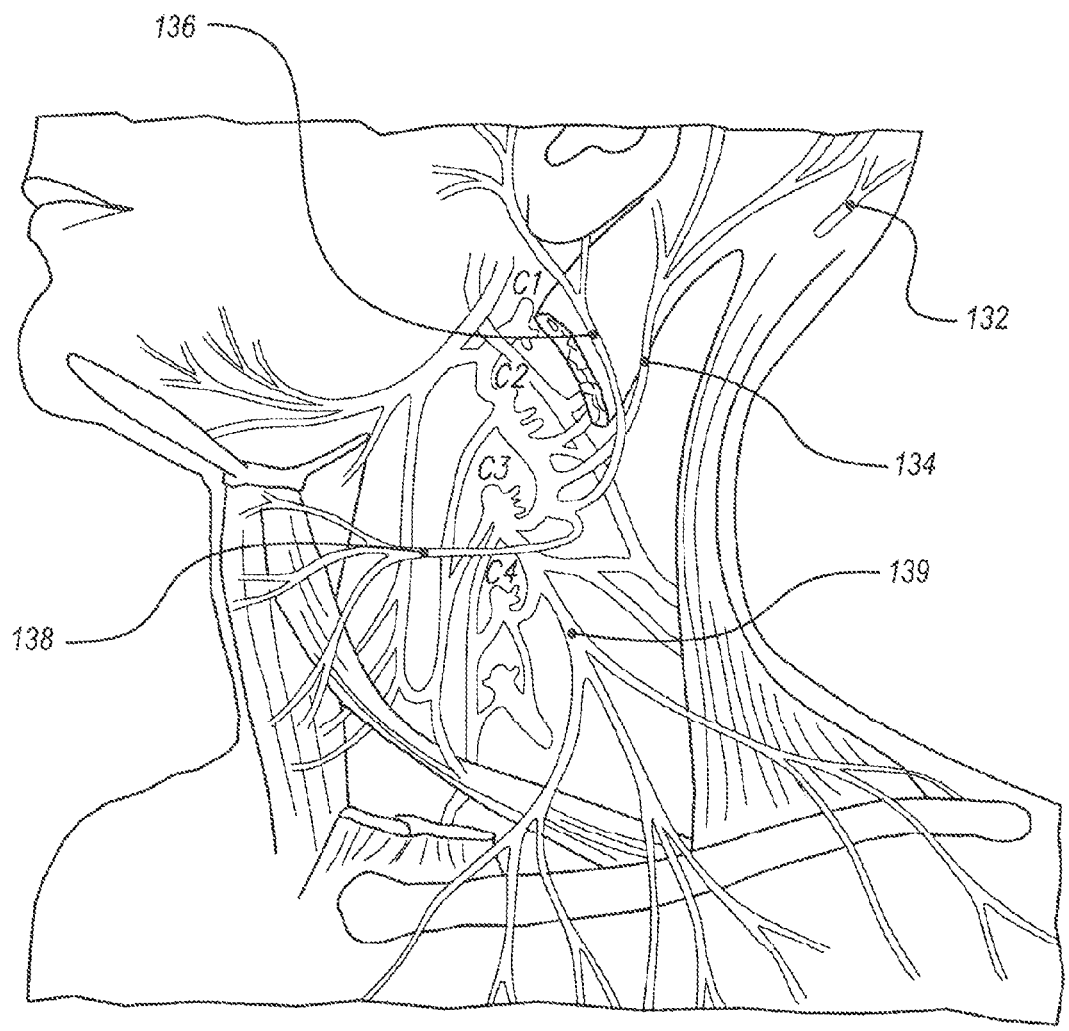
FIG. 1A depicts the upper cervical spine area of a patient and shows a number of nerves originating in the upper cervical spine area.

FIG. 1A depicts the upper cervical spine (C1-C4) area of a patient. As shown in FIG. 1A, a number of nerves arise from the upper cervical spine (C1-C4). Examples of such nerves include, but are not limited to, the greater occipital nerve(s) (132), lesser occipital nerve(s) (134), greater auricular nerve(s) (136), transverse cervical nerve(s) (138), supraclavicular nerve(s) (139), and/or branches of any of these nerves.

Figure 1B:
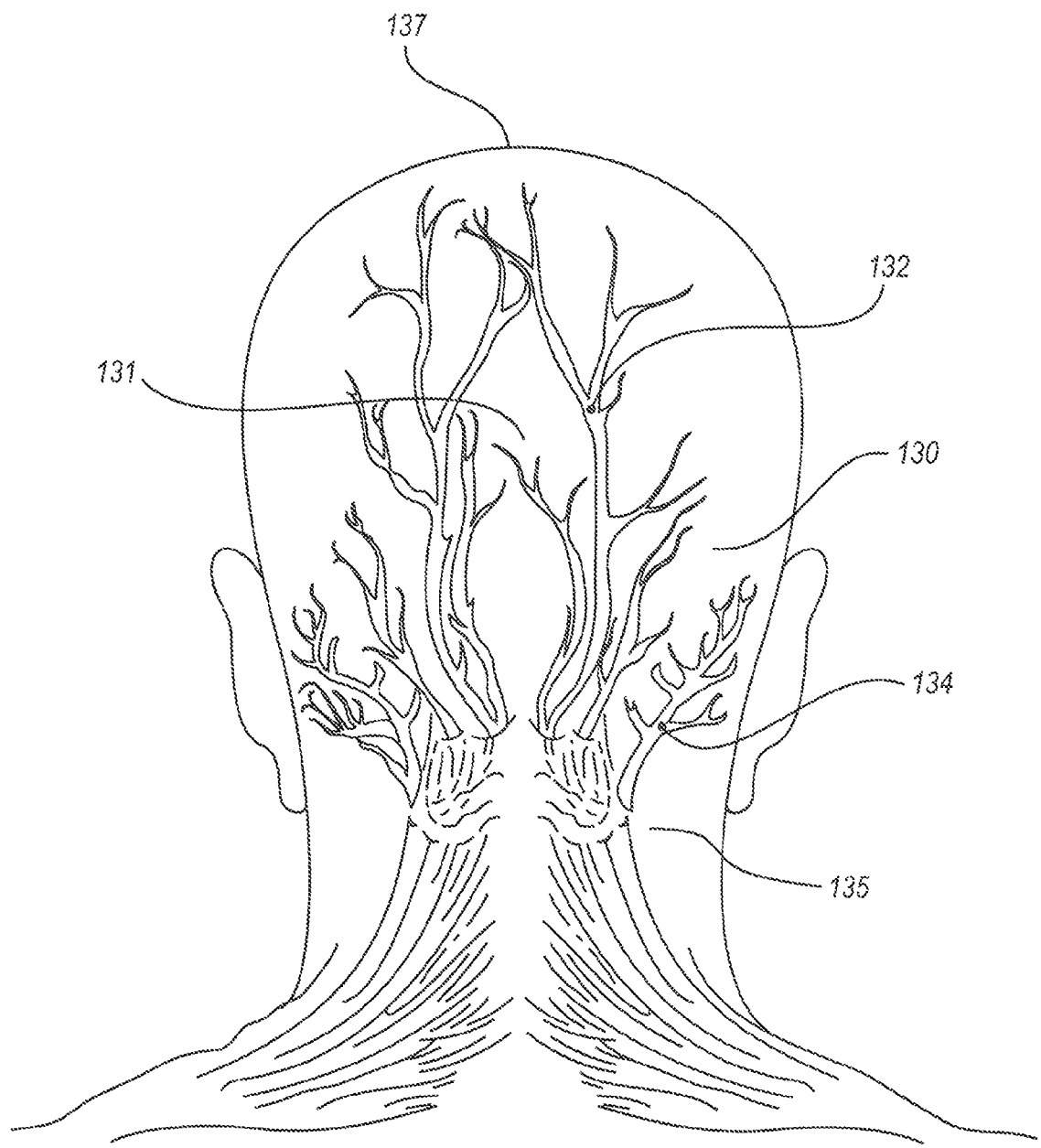
FIG. 1B depicts the occipital nerves in the back of the head and upper neck area of a patient.

FIG. 1B depicts the occipital nerves (130) in the back of the head and upper neck area of a patient. As shown in FIG. 1B, the occipital nerves (130) are divided into greater (132) and lesser (134) occipital nerves. The occipital nerves (130) lie subcutaneously in the back of the head and upper neck and are therefore are relatively easily accessed. Thus, as will be described in more detail below, a stimulator and/or electrode lead may be implanted in the back of the head or upper neck to provide a stimulus to the occipital nerves (130).

Figure 1C:
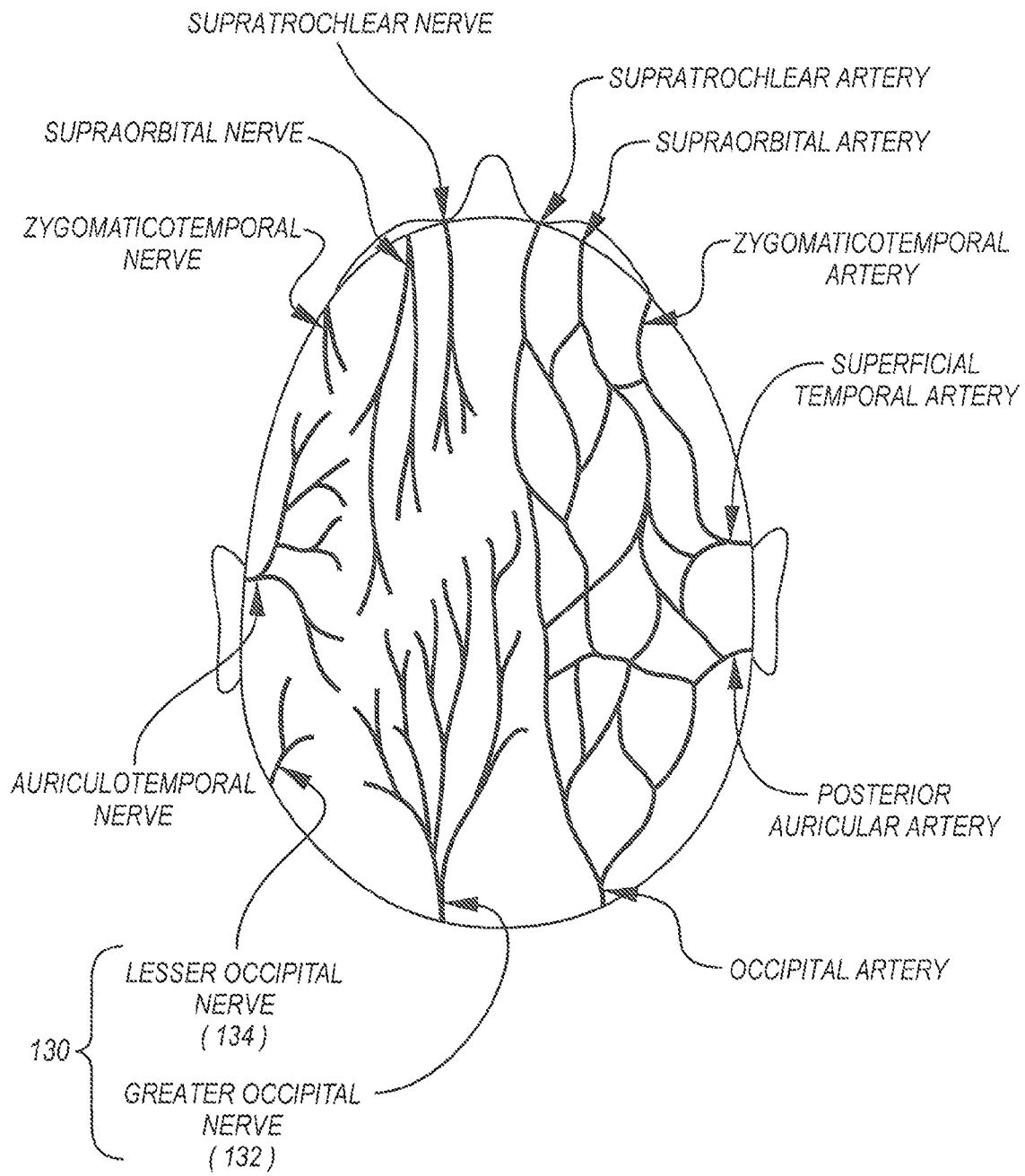
FIG. 1C illustrates a view of the major nerves and arteries in the human head as viewed from above looking down on the top or superior part of the head.

FIG. 1C illustrates a view of the major nerves and arteries in the human head as viewed from above looking down on the top or superior part of the head. As shown in FIG. 1C, the greater occipital nerves (132) extend to and across some of the top or superior portion of the head. The lesser occipital nerves (134) may also extend to or near the top or superior portion of the head. Consequently, as will be described in more detail below, an implanted stimulator or an electrode lead can be located along the back or posterior part of the head or on the top or superior portion of the head and still provide a stimulus to the occipital nerves (130).

It has been discovered that stimulating one or more of the nerves in the head with an electrical stimulation current can alleviate or eliminate headache pain for patients who do not respond to other forms of treatment or who do not prefer any of the other forms of treatment. This includes migraine headaches.

Consequently, a stimulator may be implanted in a patient to deliver an electrical stimulation current to one or more of the nerves in the head, particularly the occipital nerves (130). This stimulation may be effective to treat headache pain and other types of pain or conditions, such as occipital neuralgia, facial pain, etc. The present specification will describe methods and systems for implanting such a stimulator to most conveniently treat a variety of conditions, particularly headaches.

As used herein, and in the appended claims, the term "stimulator" will be used broadly to refer any device that delivers a stimulus, such as an electrical stimulation current, one or more drugs, chemical stimulation, thermal stimulation, electromagnetic stimulation, mechanical stimulation, and/or any other suitable stimulation to a stimulation site. Thus, the term "stimulator" includes, but is not limited to, a stimulator, microstimulator, implantable pulse generator (IPG), system control unit (stimulator) or similar device. The stimulation site referred to herein is the occipital nerve (130) for illustrative purposes only. However, it will be recognized that the stimulation site may additionally or alternatively include any nerve, tissue, blood vessel, or other area within the patient.

Figure 2:
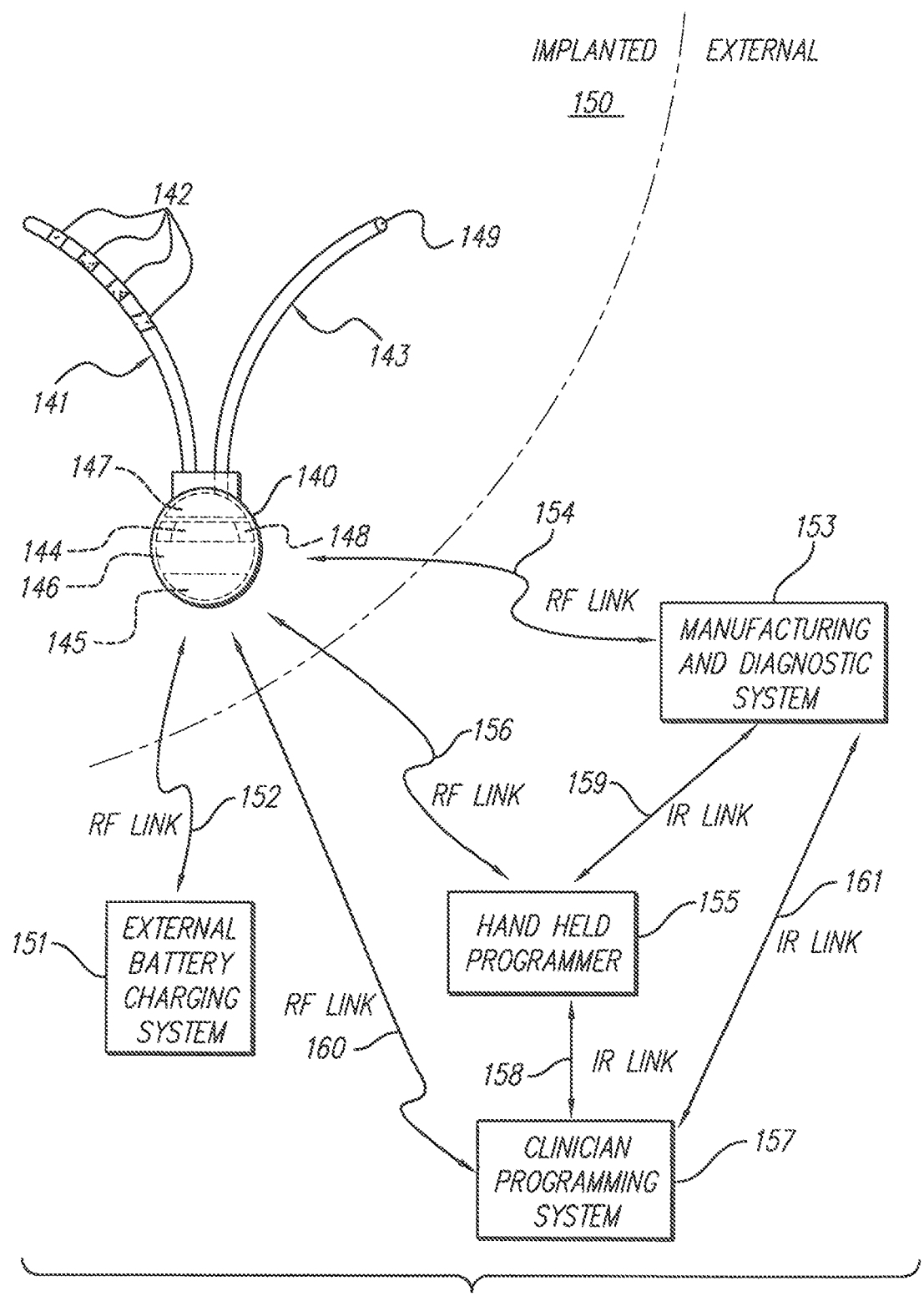
FIG. 2 illustrates an exemplary stimulator that may be used to apply a stimulus to a target nerve to treat a particular medical condition according to principles described herein.

To facilitate an understanding of the methods of optimally placing a stimulator to treat headache pain and other conditions, as described herein, a more detailed description of the stimulator and its operation will now be given with reference to the figures. FIG. 2 illustrates an exemplary stimulator (140) that may be implanted within a patient (150) and used to apply a stimulus to a stimulation site, e.g., an electrical stimulation of the stimulation site, an infusion of one or more drugs into the stimulation site, or both. The electrical stimulation function of the stimulator (140) will be described first, followed by an explanation of the drug delivery function of the stimulator (140). It will be understood, however, that the stimulator (140) may be configured to provide any type of stimulation as best suits a particular patient.

The exemplary stimulator (140) shown in FIG. 2 is configured to provide electrical stimulation to a stimulation site within a patient and includes a lead (141) having a proximal end coupled to the body of the stimulator (140). The lead (141) also includes a number of electrodes (142) configured to apply an electrical stimulation current to a stimulation site. In some embodiments, the lead (141) includes anywhere between two and sixteen electrodes (142). However, the lead (141) may include any number of electrodes (142) as best serves a particular application. The electrodes (142) may be arranged as an array, for example, having at least two or at least four collinear electrodes. In some embodiments, the electrodes are alternatively inductively coupled to the stimulator (140). The lead (141) may be thin (e.g., less than 3 millimeters in diameter) such that the lead (141) may be positioned near a stimulation site.

As illustrated in FIG. 2, the stimulator (140) includes a number of components. It will be recognized that the stimulator (140) may include additional and/or alternative components as best serves a particular application. A power source (145) is configured to output voltage used to supply the various components within the stimulator (140) with power and/or to generate the power used for electrical stimulation. The power source (145) may be a primary battery, a rechargeable battery, super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like. Alternatively, the stimulator (140) may include one or more components configured to receive power from another medical device that is implanted within the patient.

When the power source (145) is a battery, it may be a lithium-ion battery or other suitable type of battery. When the power source (145) is a rechargeable battery, it may be recharged from an external system through a power link such as a radio frequency (RF) power link. One type of rechargeable battery that may be used is described in International Publication WO 01/82398 A1, published Nov. 1, 2001, and/or WO 03/005465 A1, published Jan. 16, 2003, both of which are incorporated herein by reference in their entireties. Other battery construction techniques that may be used to make a power source (145) include those shown, e.g., in U.S. Pat. Nos. 6,280,873; 6,458,171, and U.S. Publications 2001/0046625 A1 and 2001/0053476 A1, all of which are incorporated herein by reference in their entireties. Recharging can be performed using an external charger.

The stimulator (140) may also include a coil (148) configured to receive and/or emit a magnetic field (also referred to as a radio frequency (RF) field) that is used to communicate with or receive power from one or more external devices (151, 153, 155). Such communication and/or power transfer may include, but is not limited to, transcutaneously receiving data from the external device, transmitting data to the external device, and/or receiving power used to recharge the power source (145).

For example, an external battery charging system (EBCS) (151) may provide power used to recharge the power source (145) via an RF link (152). External devices including, but not limited to, a hand held programmer (HHP) (155), clinician programming system (CPS) (157), and/or a manufacturing and diagnostic system (MDS) (153) may be configured to activate, deactivate, program, and test the stimulator (140) via one or more RF links (154, 156). It will be recognized that the links, which are RF links (152, 154, 156) in the illustrated example, may be any type of link used to transmit data or energy, such as an optical link, a thermal link, or any other energy-coupling link. One or more of these external devices (153, 155, 157) may also be used to control the infusion of one or more drugs into a stimulation site to treat headaches and other conditions.

Additionally, if multiple external devices are used in the treatment of a patient, there may be some communication among those external devices, as well as with the implanted stimulator (140). Again, any type of link for transmitting data or energy may be used among the various devices illustrated. For example, the CPS (157) may communicate with the HHP (155) via an infrared (IR) link (158), with the MDS (153) via an IR link (161), and/or directly with the stimulator (140) via an RF link (160). As indicated, these communication links (158, 161, 160) are not necessarily limited to IR and RF links and may include any other type of communication link. Likewise, the MDS (153) may communicate with the HHP (155) via an IR link (159) or via any other suitable communication link.

The HHP (155), MDS (153), CPS (157), and EBCS (151) are merely illustrative of the many different external devices that may be used in connection with the stimulator (140). Furthermore, it will be recognized that the functions performed by any two or more of the HHP (155), MDS (153), CPS (157), and EBCS (151) may be performed by a single external device. One or more of the external devices (153, 155, 157) may be embedded in a seat cushion, mattress cover, pillow, garment, belt, strap, pouch, or the like so as to be positioned near the implanted stimulator (140) when in use.

The stimulator (140) may also include electrical circuitry (144) configured to produce electrical stimulation pulses that are delivered to the stimulation site via the electrodes (142). In some embodiments, the stimulator (140) may be configured to produce monopolar stimulation. The stimulator (140) may alternatively or additionally be configured to produce bipolar stimulation. Monopolar electrical stimulation is achieved, for example, using the stimulator case as an indifferent electrode. Bipolar electrical stimulation is achieved, for example, using one of the electrodes of the electrode array as an indifferent electrode. The electrical circuitry (144) may include one or more processors configured to decode stimulation parameters and generate the stimulation pulses. In some embodiments, the stimulator (140) has at least four channels and drives up to sixteen electrodes or more. The electrical circuitry (144) may include additional circuitry such as capacitors, integrated circuits, resistors, coils, and the like configured to perform a variety of functions as best serves a particular application.

The stimulator (140) may also include a programmable memory unit (146) for storing one or more sets of data and/or stimulation parameters. The stimulation parameters may include, but are not limited to, electrical stimulation parameters, drug stimulation parameters, and other types of stimulation parameters. The programmable memory (146) allows a patient, clinician, or other user of the stimulator (140) to adjust the stimulation parameters such that the stimulation applied by the stimulator (140) is safe and efficacious for treatment of a particular patient with chronic headaches or any other condition being treated. The different types of stimulation parameters (e.g., electrical stimulation parameters and drug stimulation parameters) may be controlled independently. However, in some instances, the different types of stimulation parameters are coupled. For example, electrical stimulation may be programmed to occur only during drug stimulation. Alternatively, the different types of stimulation may be applied at different times or with only some overlap. The programmable memory (146) may be any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, electrode configuration (i.e., anode-cathode assignment), burst pattern (e.g., burst on time and burst off time), duty cycle or burst repeat interval, ramp on time, and ramp off time of the stimulation current that is applied to the stimulation site. The drug stimulation parameters may control various parameters including, but not limited to, the amount of drugs infused into the stimulation site, the rate of drug infusion, and the frequency of drug infusion. For example, the drug stimulation parameters may cause the drug infusion rate to be intermittent, constant, or bolus. Other stimulation parameters that characterize other classes of stimuli are possible. For example, when tissue is stimulated using electromagnetic radiation, the stimulation parameters may characterize the intensity, wavelength, and timing of the electromagnetic radiation stimuli. When tissue is stimulated using mechanical stimuli, the stimulation parameters may characterize the pressure, displacement, frequency, and timing of the mechanical stimuli.

Specific stimulation parameters may have different effects on different types of medical conditions. Thus, in some embodiments, the stimulation parameters may be adjusted by the patient, a clinician, or other user of the stimulator (140) as best serves a particular medical condition. The stimulation parameters may also be automatically adjusted by the stimulator (140), as will be described below. For example, the amplitude of the stimulus current applied to a stimulation site may be adjusted to have a relatively low value to target relatively large diameter fibers of a stimulation site. The stimulator (140) may also increase excitement of a stimulation site by applying a stimulation current having a relatively low frequency to the stimulation site (e.g., less than 100 Hz). The stimulator (140) may also decrease excitement of a stimulation site by applying a relatively high frequency to the stimulation site (e.g., greater than 100 Hz). The stimulator (140) may also be programmed to apply the stimulation current to a stimulation site intermittently or continuously.

Additionally, the exemplary stimulator (140) shown in FIG. 2 is configured to provide drug stimulation to a patient, for example, a headache patient, by applying one or more drugs to a stimulation site. For this purpose, a pump (147) may also be included within the stimulator (140). The pump (147) is configured to store and dispense one or more drugs, for example, through a catheter (143). The catheter (143) is coupled at a proximal end to the stimulator (140) and may have an infusion outlet (149) for infusing dosages of the one or more drugs into a predetermined site within a stimulation site. In some embodiments, the stimulator (140) may include multiple catheters (143) and/or pumps (147) for storing and infusing dosages of the one or more drugs into predetermined sites within the stimulation site.

The pump (147) or controlled drug release device described herein may include any of a variety of different drug delivery systems. Controlled drug release devices based upon a mechanical or electromechanical infusion pump may be used. In other examples, the controlled drug release device can include a diffusion-based delivery system, e.g., erosion-based delivery systems (e.g., polymer-impregnated with drug placed within a drug-impermeable reservoir in communication with the drug delivery conduit of a catheter), electrodiffusion systems, and the like. Another example is a convective drug delivery system, e.g., systems based upon electroosmosis, vapor pressure pumps, electrolytic pumps, effervescent pumps, piezoelectric pumps and osmotic pumps. Another example is a micro-drug pump.

Exemplary pumps (147) or controlled drug release devices suitable for use as described herein include, but are not necessarily limited to, those disclosed in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like. Additional exemplary drug pumps suitable for use as described herein include, but are not necessarily limited to, those disclosed in U.S. Pat. Nos. 4,562,751; 4,678,408; 4,685,903; 5,080,653; 5,097,122; 6,740,072; and 6,770,067. Exemplary micro-drug pumps suitable for use as described herein include, but are not necessarily limited to, those disclosed in U.S. Pat. Nos. 5,234,692; 5,234,693; 5,728,396; 6,368,315; 6,666,845; and 6,620,151. All of these listed patents are incorporated herein by reference in their respective entireties.

The stimulator (140) of FIG. 2 is illustrative of many types of stimulators that may be used to stimulate the occipital nerves and other target sites to treat headaches and other conditions. For example, the stimulator (140) may include an implantable pulse generator (IPG) coupled to one or more leads having a number of electrodes, a spinal cord stimulator (SCS), a cochlear implant, a deep brain stimulator, a drug pump (mentioned previously), a micro-drug pump (mentioned previously), or any other type of implantable stimulator configured to deliver a stimulus to a stimulation site within a patient. Exemplary IPGs suitable for use as described herein include, but are not limited to, those disclosed in U.S. Pat. Nos. 6,381,496, 6,553,263; and 6,760,626. Exemplary spinal cord stimulators suitable for use as described herein include, but are not limited to, those disclosed in U.S. Pat. Nos. 5,501,703; 6,487,446; and 6,516,227. Exemplary cochlear implants suitable for use as described herein include, but are not limited to, those disclosed in U.S. Pat. Nos. 6,219,580; 6,272,382; and 6,308,101. Exemplary deep brain stimulators suitable for use as described herein include, but are not limited to, those disclosed in U.S. Pat. Nos. 5,938,688; 6,016,449; and 6,539,263. All of these listed patents are incorporated herein by reference in their respective entireties.

Alternatively, the stimulator (140) may include an implantable microstimulator, such as a BION® microstimulator (Advanced Bionics® Corporation, Valencia, Calif.). Various details associated with the manufacture, operation, and use of implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

Figure 3:
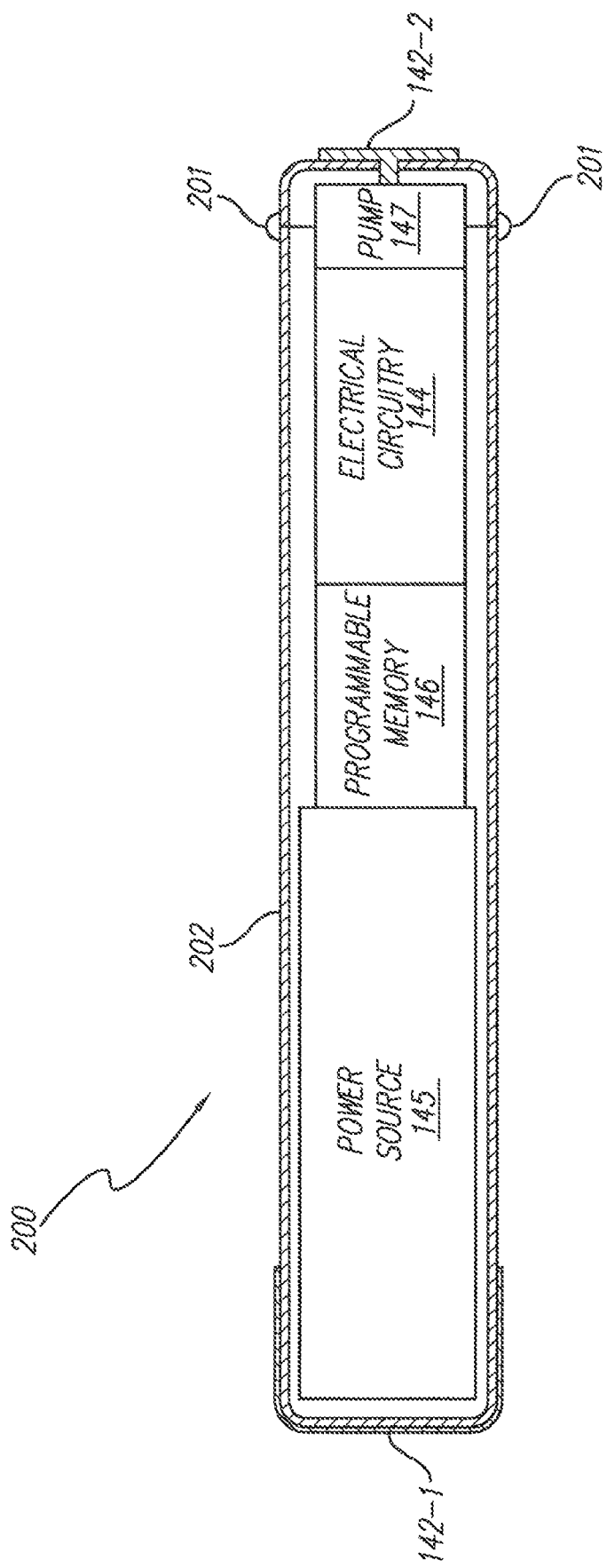
FIG. 3 illustrates an exemplary microstimulator that may be used as the stimulator according to principles described herein.

FIG. 3 illustrates an exemplary microstimulator (200) that may be used as the stimulator (140; FIG. 2) described herein. Other configurations of the microstimulator (200) are possible, as shown in the above-referenced patents and as described further below.

As shown in FIG. 3, the microstimulator (200) may include the power source (145), the programmable memory (146), the electrical circuitry (144), and the pump (147) described in connection with FIG. 2. These components are housed within a capsule (202). The capsule (202) may be a thin, elongated cylinder or any other shape as best serves a particular application. The shape of the capsule (202) may be determined by the structure of the desired target nerve, the surrounding area, and the method of implementation. In some embodiments, the capsule (202) is substantially equal to or less than three cubic centimeters.

In some embodiments, the microstimulator (200) may include two or chore leadless electrodes (142). Either or both of the electrodes (142) may alternatively be located at the ends of short, flexible leads as described in U.S. patent application Ser. No. 09/624,130, filed Jul. 24, 2000, which is incorporated herein by reference in its entirety. The use of such leads permits, among other things, electrical stimulation to be directed more locally to targeted tissue(s) a short distance from the surgical fixation of the bulk of the microstimulator (200), while allowing most elements of the microstimulator (200) to be located in a more surgically convenient site. This minimizes the distance traversed and the surgical planes crossed by the microstimulator (200) and any lead(s).

The external surfaces of the microstimulator (200) may advantageously be composed of biocompatible materials. For example, the capsule (202) may be made of glass, ceramic, metal, or any other material that provides a hermetic package that will exclude water vapor but permit passage of electromagnetic fields used to transmit data and/or power. The electrodes (142) may be made of a noble or refractory metal or compound, such as platinum, iridium, tantalum, titanium, titanium nitride, niobium or alloys of any of these, in order to avoid corrosion or electrolysis which could damage the surrounding tissues and the device.

The microstimulator (200) may also include one or more infusion outlets (201). The infusion outlets (201) facilitate the infusion of one or more drugs into a treatment site to treat a particular medical condition. The infusion outlets (201) may dispense one or drugs directly to the treatment site. Alternatively, as will be described in more detail below, catheters may be coupled to the infusion outlets (201) to deliver the drug therapy to a treatment site some distance from the body of the microstimulator (200). The stimulator (200) of FIG. 3 also includes electrodes (142-1 and 142-2) at either end of the capsule (202). One of the electrodes (142) may be designated as a stimulating electrode to be placed close to the treatment site and one of the electrodes (142) may be designated as an indifferent electrode used to complete a stimulation circuit.

The microstimulator (200) may be implanted within a patient with a surgical tool such as a hypodermic needle, bore needle, or any other tool specially designed for the purpose. Alternatively, the microstimulator (200) may be implanted using endoscopic or laparoscopic techniques.

Figure 4:
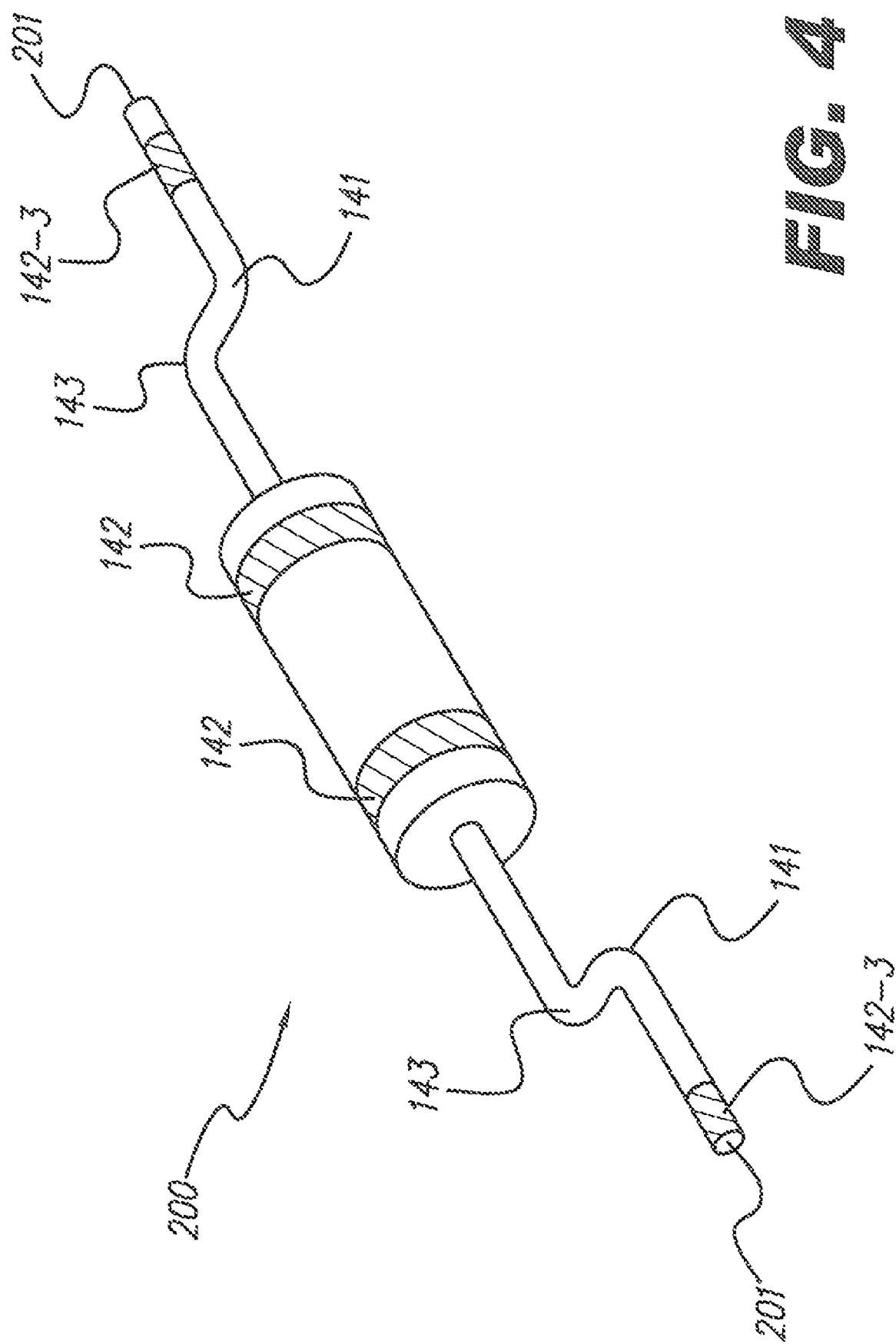
FIG. 4 shows one or more catheters coupled to the microstimulator according to principles described herein.

FIG. 4 shows an example of a microstimulator (200) with one or more catheters (143) coupled to the infusion outlets on the body of the microstimulator (200). With the catheters (143) in place, the infusion outlets (201) that actually deliver the drug therapy to target tissue are located at the ends of catheters (143). Thus, in the example of FIG. 4, a drug therapy is expelled by the pump (147, FIG. 3) from an infusion outlet (201, FIG. 3) in the casing (202, FIG. 3) of the microstimulator (200), through the catheter (143), out an infusion outlet (201) at the end of the catheter (143) to the stimulation site within the patient. As shown in FIG. 4, the catheters (143) may also serve as leads (141) having one or more electrodes (142-3) disposed thereon. Thus, the catheters (143) and leads (141) of FIG. 4 permit infused drugs and/or electrical stimulation current to be directed to a stimulation site while allowing most elements of the microstimulator (200) to be located in a more surgically convenient site. The example of FIG. 4 may also include leadless electrodes (142) disposed on the housing of the microstimulator (200), in the same manner described above.

Figure 5:
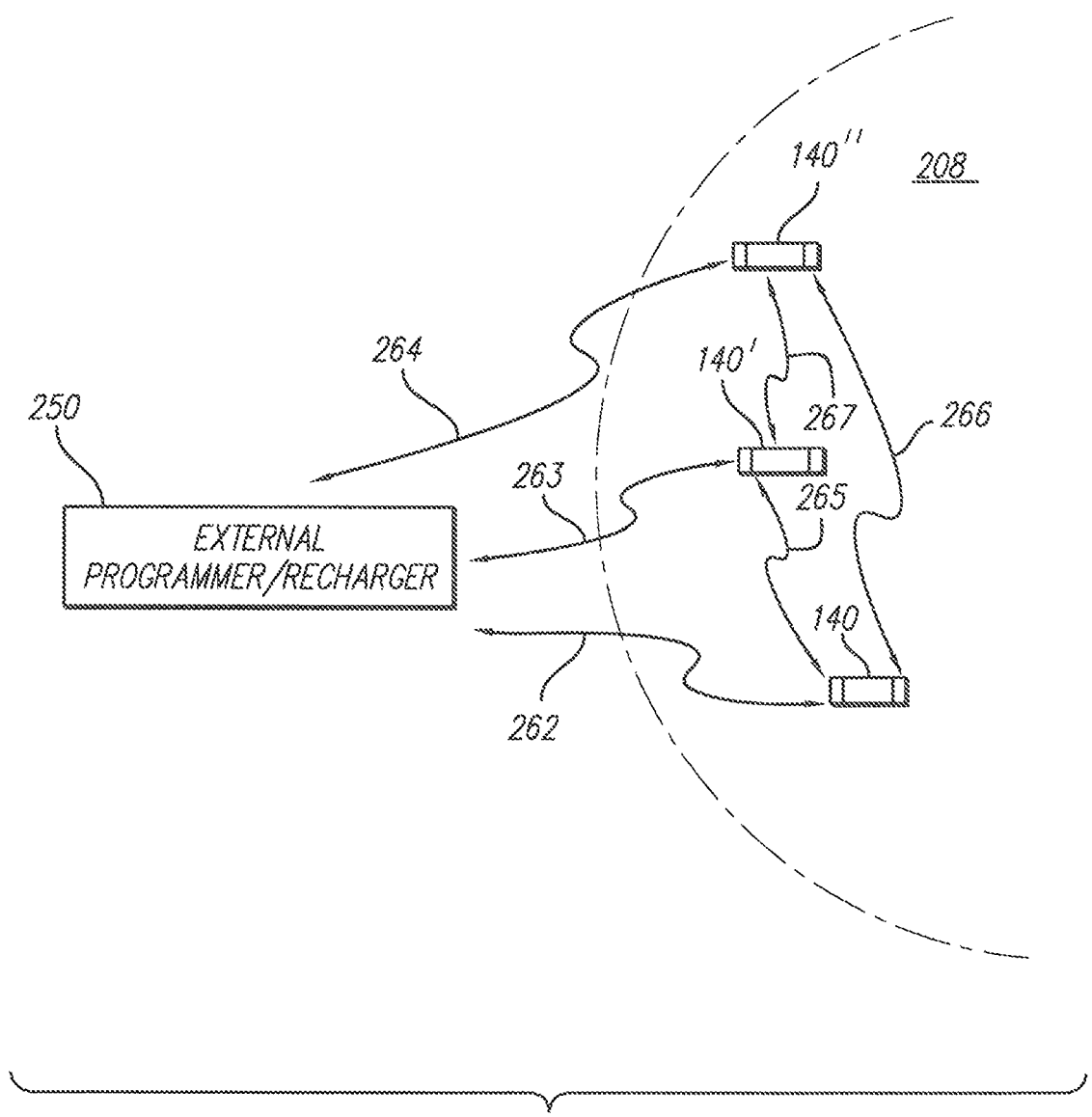
FIG. 5 depicts a number of stimulators configured to communicate with each other and/or with one or more external devices according to principles described herein.

A stimulator may be configured to operate independently. Alternatively, as shown in FIG. 5 and described in more detail below, the stimulator (140) may be configured to operate in a coordinated manner with one or more additional stimulators, other implanted devices, or other devices external to the patient's body. For instance, a first stimulator may control or operate under the control of a second stimulator, other implanted device, or other device external to the patient's body. The stimulator (140) may be configured to communicate with other implanted stimulators, other implanted devices, or other devices external to the patient's body via an RF link, an untrasonic link, an optical link, or any other type of communication link. For example, the stimulator (140) may be configured to communicate with an external remote control unit that is capable of sending commands and/or data to the stimulator (140) and that is configured to receive commands and/or data from the stimulator (140).

In order to determine the strength and/or duration of electrical stimulation and/or amount and/or type(s) of stimulating drug(s) required to most effectively treat a headache or other condition, various indicators of headache and/or a patient's response to treatment may be sensed or measured. These indicators include, but are not limited to, electrical activity of the brain (e.g., EEG); neurotransmitter levels; hormone levels; metabolic activity in the brain; blood flow rate in the head, neck or other areas of the body; medication levels within the patient; patient input, e.g. when prodromal symptoms are sensed the patient can push a button on a remote control or other external unit; temperature of tissue in stimulation target region, including the occipital nerve; physical activity level, e.g. based on accelerometer recordings; brain hyperexcitability, e.g. increased response of given tissue to the same input; indicators of collateral tissue stimulation might be used to adjust stimulation parameters; and/or detection of muscle tone in neck (mechanical strain, pressure sensor, EMG). In some embodiments, the stimulator (140) may be configured to change the stimulation parameters in a closed loop manner in response to these measurements. The stimulator (140) may be configured to perform the measurements. Alternatively, other sensing devices may be configured to perform the measurements and transmit the measured values to the stimulator (140). Exemplary sensing devices include, but are not limited to, chemical sensors, electrodes, optical sensors, mechanical (e.g., motion, pressure) sensors, and temperature sensors.

Thus, one or more external devices may be provided to interact with the stimulator (140), and may be used to accomplish at least one or more of the following functions:

Function 1: If necessary, transmit electrical power to the stimulator (140) in order to power the stimulator (140) and/or recharge the power source (145).

Function 2: Transmit data to the stimulator (140) in order to change the stimulation parameters used by the stimulator (140).

Function 3: Receive data indicating the state of the stimulator (140) (e.g., battery level, drug level, stimulation parameters, etc.).

Additional functions may include adjusting the stimulation parameters based on information sensed by the stimulator (140) or by other sensing devices.

By way of example, an exemplary method of treating a patient with a chronic headache or other condition may be carried out according to the following sequence of procedures. The steps listed below may be modified, reordered, and/or added to as best serves a particular application.

1. A stimulator (140) is implanted so that its electrodes (142) and/or infusion outlet (149) are coupled to or located near a stimulation site (e.g., the occipital nerves or other nerves in the patient's head). If the stimulator (140) is a microstimulator, such as the microstimulator (200) described in FIG. 3, the microstimulator itself may be coupled to the stimulation site.

2. The stimulator (140) is programmed to apply at least one stimulus to the stimulation site. The stimulus may include electrical stimulation, drug stimulation, chemical stimulation, thermal stimulation, electromagnetic stimulation, mechanical stimulation, and/or any other suitable stimulation.

3. When the patient desires to invoke stimulation, the patient sends a command to the stimulator (140) (e.g., via a remote control) such that the stimulator (140) delivers the prescribed stimulation. The stimulator (140) may be alternatively or additionally configured to automatically apply the stimulation in response to sensed indicators of headache or other patient condition.

4. To cease stimulation, the patient may turn off the stimulator (140) (e.g., via a remote control).

5. Periodically, the power source (145) of the stimulator (140) is recharged, if necessary, in accordance with Function 1 described above. As will be described below, this recharging function can be made much more efficient using the principles disclosed herein.

In other examples, the treatment administered by the stimulator (140), i.e., drug therapy and/or electrical stimulation, may be automatic and not controlled or invoked by the patient.

For the treatment of different patients with chronic headache or other conditions, it may be desirable to modify or adjust the algorithmic functions performed by the implanted and/or external components, as well as the surgical approaches. For example, in some situations, it may be desirable to employ more than one stimulator (140), each of which could be separately controlled by means of a digital address. Multiple channels and/or multiple patterns of stimulation may thereby be used to deal with the various components of a headache condition, such as the combination of migraine with another form or forms of headache or the combination of headache with facial or other pain.

As shown in the example of FIG. 5, a first stimulator (140) implanted beneath the skin of the patient (208) provides a stimulus to a first location; a second stimulator (140') provides a stimulus to a second location; and a third stimulator (140") provides a stimulus to a third location. As mentioned earlier, the implanted devices may operate independently or may operate in a coordinated manner with other implanted devices or other devices external to the patient's body. That is, an external controller (250) may be configured to control the operation of each of the implanted devices (140, 140', and 140"). In some embodiments, an implanted device, e.g. stimulator (140), may control or operate under the control of another implanted device(s), e.g. stimulator (140') and/or stimulator (140"). Control lines (262-267) have been drawn in FIG. 5 to illustrate that the external controller (250) may communicate or provide power to any of the implanted devices (140, 140', and 140") and that each of the various implanted devices (140, 140', and 140") may communicate with and, in some instances, control any of the other implanted devices.

As a further example of multiple stimulators (140) operating in a coordinated manner, the first and second stimulators (140, 140') of FIG. 5 may be configured to sense various indicators of a headache or other condition and transmit the measured information to the third stimulator (140"). The third stimulator (140") may then use the measured information to adjust its stimulation parameters and apply stimulation to a stimulation site accordingly (e.g., to the occipital nerves). The various implanted stimulators may, in any combination, sense indicators of headache or other conditions, communicate or receive data on such indicators, and adjust stimulation parameters accordingly.

Alternatively, the external device (250) or other external devices communicating with the external device may be configured to sense various indicators of a patient's condition. The sensed indicators can then be collected by the external device (250) for relay to one or more of the implanted stimulators or may be transmitted directly to one or more of the implanted stimulators by any of an array of external sensing devices. In either case, the stimulator, upon receiving the sensed indicator(s), may adjust stimulation parameters accordingly. In other examples, the external controller (250) may determine whether any change to stimulation parameters is needed based on the sensed indicators. The external device (250) may then signal a command to one or more of the stimulators to adjust stimulation parameters accordingly.

The nerve or nerves stimulated to treat headache pain include, for example, but are not limited to, any cranial nerve; the greater, lesser or third occipital nerves; the trigeminal nerve; the infraorbital nerve; the facial nerve; the maxillary nerve, the mandibular nerve and divisions of those nerves such as the two branches of the ophthalmic division of the trigeminal nerve, i.e., the supratrochlear and suprorbital nerves; the zygomaticotemporal nerve branching from the maxillary division of the trigeminal nerve; and the auriculotemporal nerve branching from the mandibular division of the trigeminal nerve. However, stimulation of the occipital nerves has been shown to be particularly effective in treating chronic headache pain.

As described above, implanting a stimulator to provide an electrical stimulation to the occipital nerves has been known to create a paresthesia at the stimulation site. Consequently, such stimulation may be used to treat conditions such as occipital neuralgia as described in U.S. Pat. No. 6,505,075 to Weiner, which is incorporated herein by reference in its entirety.

In addition to creating a local paresthesia, stimulation of the occipital nerves has also been shown to have a therapeutic effect on headache pain that may or may not have any demonstrable connection with the occipital nerves. This is true of both migraine and other forms of chronic headaches.

Hence, as will be described in more detail below, one or more stimulating leads may be implanted adjacent to or near one or more of the occipital nerves. With reference to FIGS. 1B and 1C, the leads may be implanted in the patient's neck at or near the base of the skull (135), at the back of the head (131), on the top or superior portion of the skull (137), or at any other suitable location.

However, one of the issues with using a stimulator and lead to stimulate a stimulation site (e.g., the occipital nerves) within the brain is lead migration. Implanted stimulators are implanted, generally, on a long-term or permanent basis. However, with time and the natural movement of the patient, a lead from an implanted stimulator tends to move away from the location where it was first implanted. For example, a simple nod of the head may cause the position of a lead that is implanted in the neck to shift positions. This tendency is known as lead migration, or simply, migration.

Figure 6:
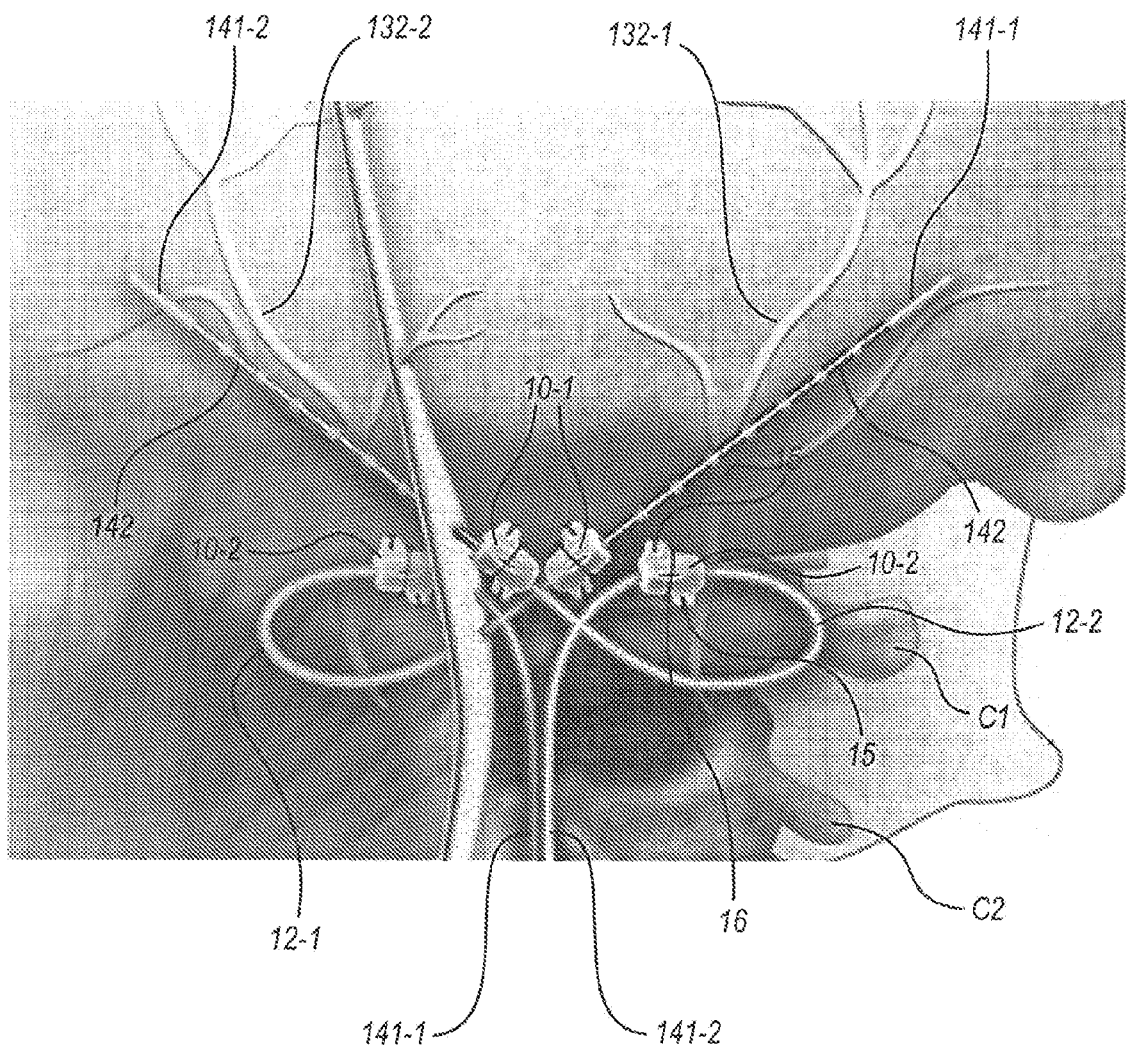
FIG. 6 illustrates an exemplary stimulation system wherein two leads are implanted adjacent to one or more of the occipital nerves according to principles described herein.

FIG. 6 illustrates an exemplary stimulation system wherein two leads (141) are implanted adjacent to one or more of the occipital nerves (130). Although the following examples will describe methods and systems of preventing mitigation of leads (141), it will be recognized that the methods and systems described herein may be applied to catheters or other devices configured to deliver a stimulus to a stimulation site within the neck or head of a patient.

Two leads (141) may be used for a number of reasons. For example, it is often desirable to stimulate a number of nerves (e.g., the greater and lesser occipital nerves on both the right and left sides of the patient) with the leads (141). However, the distance of the greater (132) and lesser (134; FIG. 1B) occipital nerves from the midline (the vertical plane that divides the body into right and left sides) varies from patient to patient. Hence, a single lead may not be long enough to cover both the greater (132) and lesser (134; FIG. 1B) occipital nerves. However, it will be recognized that a single lead (141) or three or more leads (141) may alternatively be used in connection with the methods and systems described herein.

As shown in FIG. 6, the first lead (141-1) is placed over the greater occipital nerve (132-1) on the right side of the patient and the second lead (141-2) is placed over the greater occipital nerve (132-2) on the left side of the patient. Each lead (141) may additionally or alternatively be placed over any other stimulation site (e.g., the lesser occipital nerve). In some examples, the distal tip of each of the leads (141) is placed four to five centimeters from the midline to minimize the need to advance the leads (141) following insertion. However, it will be recognized that the leads (141) may be placed any distance from the midline.

As shown in FIG. 6, a number of electrodes (142) may be disposed on each lead (141). The number of electrodes (142) may vary as best serves a particular application and lead size. For example, as shown in FIG. 6, each lead (141) may include eight electrodes (142).

Each electrode (142) may be selectively programmed to assume a positive (anode), negative (cathode), or OFF polarity to create a particular stimulation field when current is applied. Thus, different combinations of programmed anode and cathode electrode contacts may be used to deliver a variety of current waveforms to stimulate tissue surrounding the electrode contacts (142). Moreover, any of the other stimulation parameters (e.g., frequency, pulse width, amplitude, burst pattern, duty cycle, ramp on time, and ramp off time) of the stimulation current delivered by each of the electrodes (142) may be individually programmed. In this manner, as will be described in more detail below, current steering (also referred to as neuronavigation or e-trolling) may be used after the leads (141) are implanted to tailor the stimulation to the needs of a particular patient.

The leads (141) are shown in FIG. 6 to be implanted over the patient's neck at or near the base of the skull in the C1 region. The leads (141) may additionally or alternatively be implanted over the scalp of the patient or at any other suitable location.

Figure 7A:
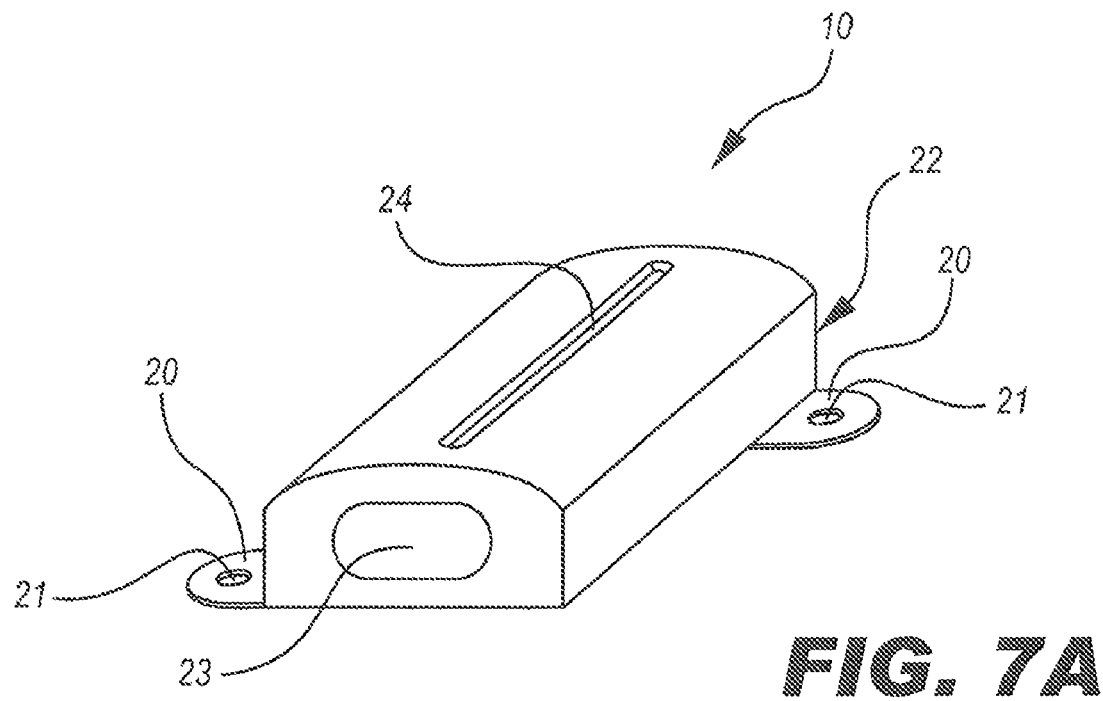
FIG. 7A is a perspective view of an exemplary suture sleeve according to principles described herein.
Figure 7B:
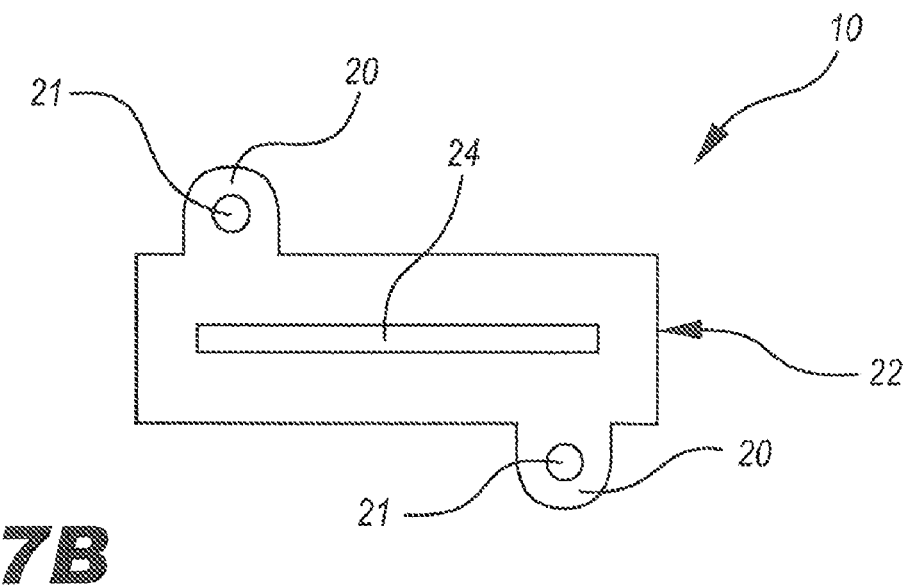
FIG. 7B is a top view of the suture sleeve illustrated in FIG. 7A according to principles described herein.

A number of suture sleeves (10) may be used to secure the leads (141) at a particular location. FIG. 7A is a perspective view of an exemplary suture sleeve (10) and FIG. 7B is a top view of the suture sleeve (10) illustrated in FIG. 7A. As shown in FIG. 7A, the sleeve (10) includes a main body (22) with a lumen (23) extending therethrough. The lead (141; FIG. 6) is configured to pass through the lumen (23).

As shown in FIGS. 7A-7B, one or more slits (24) may be included along the main body (22) of the suture sleeve (10) through which an adhesive may be inserted into the lumen (23) to secure the lead (141) to the suture sleeve (10). In some examples, the adhesive is initially in a liquid state and solidifies upon being inserted into the lumen (23). Hence, the adhesive minimizes the risk of lead slippage or migration. Any suitable surgical adhesive may be used including, but not limited to, cyanoacrylate, Duraseal™, TRUFILL® n-BCA, BioGlue™ Surgical Adhesive, and Med A.

The slit (24) also serves to prevent bunching as a suture is tied around the main body (22) of the suture sleeve (10). The suture that is tied around the main body (22) of the suture sleeve (10) will be described in more detail below.

FIGS. 7A-7B show that the suture sleeve (10) may include a number of wing members (20) extending away from the main body (22). Each of the wing members (20) includes a hole (21) through which a suture can be sewn to secure the suture sleeve (10) in place, for example, to fascia. The suture sleeve (10) shown in FIGS. 7A-7B includes two wing members (20) for illustrative purposes only. It will be recognized that any number of wing members (20) may be included through which sutures may be sewn to anchor the suture sleeve (10) in place. Additionally or alternatively, the suture sleeve (10) may include one or more anchors, hooks, adhesives, or other securing devices that are configured to secure the suture sleeve (10) in place.

Figure 7C:
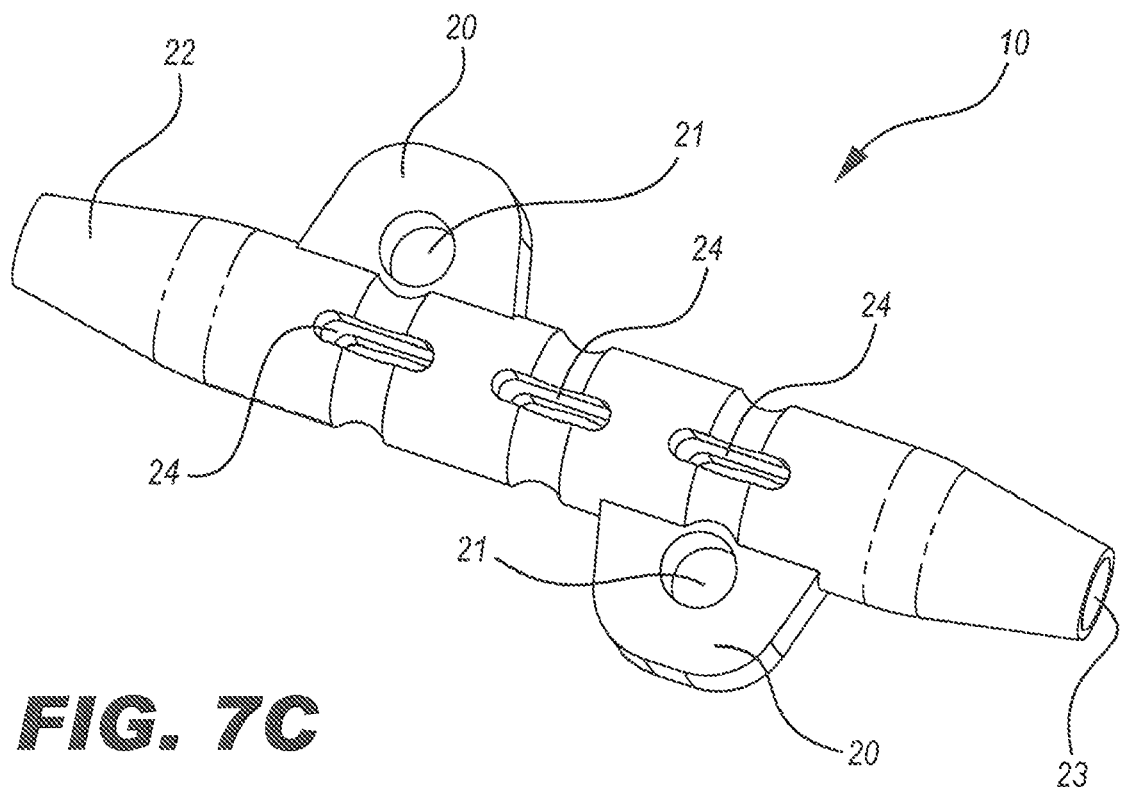
FIGS. 7C-7D show perspective views of additional exemplary suture sleeves according to principles described herein.
Figure 7D:
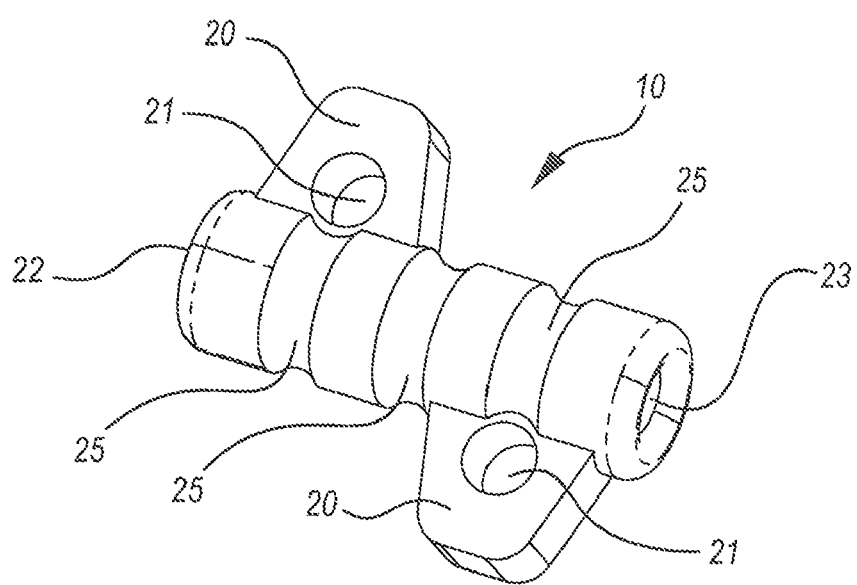

FIGS. 7C and 7D show two more exemplary suture sleeves (10) that may be used in connection with the present methods and systems. For example, the suture sleeve (10) of FIG. 7C includes the wing members (20), suture holes (21), slits (24), and lumen (23). The suture sleeve (10) of FIG. 7D alternatively does not include the slits, but rather includes a number of grooves (25). Sutures may be run along one or more of these grooves (25) to secure a lead (141; FIG. 6) in place. It will be recognized that a number of alternative designs may be used for the suture sleeves (10) as best serves a particular application.

FIG. 6 shows the suture sleeves (10) sutured into place. For example, the suture sleeve (10-2) on the right side is anchored to fascia with three sutures—two sutures (15) that pass through the holes (21; FIG. 7A) in the wing members (20; FIG. 7A) and an additional suture (16) that surrounds the main body (22; FIG. 7A) of the suture sleeve (10-2). The additional suture (16) prevents slippage of the lead (141-2) within the suture sleeve (10-2). It will be recognized that although in many applications it is advantageous to use three sutures to secure a suture sleeve (10) in place, more or less than three sutures may alternatively be used.

In some examples, the sutures are non-absorbable. Exemplary non-absorbable sutures that may be used to suture the suture sleeves (10) into place include, but are not limited to, Prolene™, Surgilene™, Nylon, Ethibond™, Mersiline™, Tevdek™, a polypropylene material, a braided polyester material, and a Teflon™ coated polyester material.

As shown in FIG. 6, each lead (141) is secured by at least two suture sleeves (10)—a distal suture sleeve (10-1) and a proximal suture sleeve (10-2). The proximal sutures sleeves (10-2) are closer to the implanted stimulator (not shown) than are the distal suture sleeves (10-1). However, it will be recognized that in some examples, each lead (141) may be secured by only one suture sleeve (10) or by three or more suture sleeves (10). For example, an additional suture sleeve (10) may be used to secure the distal tip of the lead (141). Moreover, any other securing device may additionally or alternatively be used to secure the leads (141) in place. Such securing devices may include, but are not limited to, a hook, adhesive, or anchor.

As shown in FIG. 6, the long axis of each distal suture sleeve (10-1) is substantially collinear with the long axis of the electrode region of its corresponding lead (141). The leads (141) may then extend through the distal suture sleeves (10-1) and form a loop (12) before passing through the proximal sleeves (10-2) and on to the stimulator. The portion of the lead (141) that makes up the strain relief loop (12) may be made out of any suitable material.

The loops (12) relieve strain on the lead (141) when, for example, the patient moves his or her head. This strain relief also contributes to minimize lead migration. The diameter of the strain release loops (12) may be any suitable size. Moreover, in some examples, two or more strain relief loops per lead are implemented to minimize lead migration.

As shown in FIG. 6, the long axis of each proximal suture sleeve (10-2) is substantially perpendicular to the midline or spine. It will be noted that the long axis of the proximal suture sleeves (10-2) may be oriented in any non-parallel direction with respect to the midline or spine as best serves a particular application. This placement minimizes lead migration that may be caused by the flexion or extension of the neck. Such flexion or extension of the neck may cause the proximal suture sleeve (10-2) to bend, however, the risk of the lead (141) slipping within the suture sleeve (10-2) is minimized when the proximal suture sleeve (10-2) is perpendicular to the midline or spine.

Figure 8:
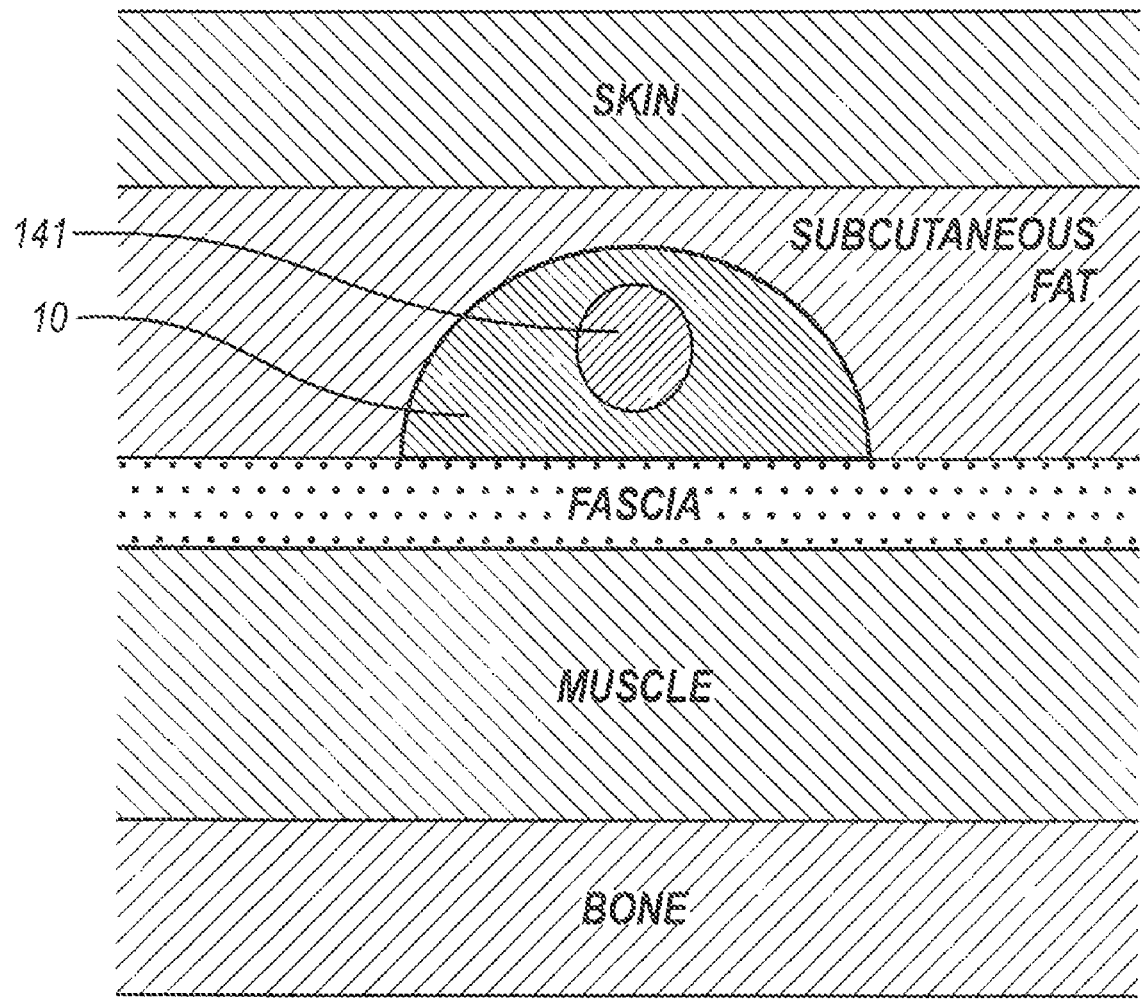
FIG. 8 is a cross-sectional end view of a subcutaneously implanted lead according to principles described herein.

Each lead (141) may be subcutaneously placed, as shown in the cross-sectional diagram of FIG. 8. FIG. 8 is a cross-sectional end view of a subcutaneously implanted lead (141). As shown in FIG. 8, a layer of muscle (31) covers bone (30) (e.g., a bone in the neck or the skull). A layer of muscle (31) covers the bone (30). The fascia (32) is a thin layer of fibrous tissue that covers the muscle (31) and separates the muscle (31) from subcutaneous fat (33). As shown in FIG. 8, the lead (141) may be implanted beneath the skin (34) in the subcutaneous fat (33) and secured to the fascia (32) via the suture sleeve (10). Alternative locations of implantation may be used for the lead (141) as best serves a particular application.

Returning to FIG. 6, each distal suture sleeve (10-1) may be sutured to fascia or any other securing site that is located in the same rostro-caudal motion segment as the most proximal electrode (142) on the lead (141) to minimize relative movement between the target nerve and distal suture sleeve (10-1). For example, if the most proximate electrode (142) to the distal suture sleeve (10-1) is located in the C2 region, the distal suture sleeve (10-1) is sutured to fascia in the same C2 region. Likewise, if the most proximate electrode (142) to the distal suture sleeve (10-1) is located in the scalp region, the distal suture sleeve (10-1) is sutured to fascia overlying the scalp.

Returning to FIG. 6, each lead (141) is coupled at its proximal end to a stimulator (140; FIG. 2). The stimulator (140; FIG. 2) may be implanted in any suitable location within the body. For example, the stimulator (140; FIG. 2) may be implanted above the iliac crest or over the ribcage to minimize the path of the leads (141) and to minimize the need for multiple lead extensions. Other exemplary implant locations may include, but are not limited to, the buttocks, neck, brain, and subcutaneous area on top of the skull, or any other suitable location within the patient.

In some examples, additional suture sleeves (10) may be used to suture the lead (141) at various locations between the proximal suture sleeves (10-2) and the implanted stimulator (140; FIG. 2). Moreover, one or more additional loops (12) may be used to further alleviate stress on the leads (141) and minimize lead migration.

A number of methods may be used to locate the optimal implantation site for the leads (141). For example, an insulated regional nerve block needle or other probe may be used to identify the location of the occipital nerve (130; FIG. 1) or other stimulation site prior to or during the implant procedure.

Additionally, the patient is usually awake and under a local anesthesia for the implantation procedure. Consequently, obtaining verbal feedback from the patient as to the effect of a trial stimulation or various stimulation parameters can be very useful in obtaining the most beneficial lead placement and stimulation current parameters. However, the patient is usually difficult to hear due to the orientation of the patient and the dressings used around the implantation procedure. Consequently, a microphone may be placed at or near the patient's mouth. The sound transduced by the microphone may be amplified and/or output through a speaker where it is clearly audible to the personnel performing the testing or implantation of the leads (141). Other patient feedback systems and methods may be used including, but not limited to, keypads, remote controls and other communication devices.

Once the leads (141) are implanted, current steering (also referred to as neuronavigation or e-trolling) may be used to tailor the stimulation to the needs of a particular patient. U.S. Pat. No. 6,393,325, which is incorporated herein by reference in its entirety, discloses an exemplary method of current steering that may be used in connection with the present methods and systems.

By way of example, another exemplary method of using current steering to optimize the stimulation parameters for a particular patient may be carried out according to the following sequence of procedures. The steps listed below may be modified, reordered, and/or added to as best serves a particular application.

1. Beginning at top of the left lead (141-2), steer down until the patient begins reporting paresthesias. Continue steering down one electrode at a time and identify where along the lead (141-2) the paresthesia is the highest and the most intense. Patient feedback and/or some other monitoring device may be used to signal where the paresthesia is the highest and most intense. Mark this location as the optimal stimulation location along this lead (141-2).

2. Repeat step 1 above for the right lead (141-1).

3. For each lead (141), evaluate the distance of the optimal electrode from the midline. If the distance is greater than 30 mm in the neck region, the optimal stimulation site is most likely the lesser occipital nerve (134; FIG. 1B).

4. If the optimal stimulation site found in step 3 is the lesser occipital nerve (134; FIG. 1B), repeat steps 1-3 to add a second stimulation site on both leads (141) which is less than 30 mm from the midline. This stimulation site covers the greater occipital nerve (132; FIG. 1B).

In some instances, it may be desirable to measure the amount of lead migration that occurs over a specific amount of time. For this purpose, a radioopaque bead may be implanted within the patient over the center of the occipital protuberance to provide a landmark in the radiographic plane of the leads. After the lead implant procedure is complete, a true AP fluoroscopic image of the leads (141) and the bead may be printed. Should lead migration be suspected in the future, a second x-ray may be taken with a bead over the occipital protuberance to allow quantitative assessment of lead migration.

The preceding description has been presented only to illustrate and describe embodiments of the invention. It is not intended to be exhaustive or to limit the invention to any precise form disclosed. Many modifications and variations are possible in light of the above teaching.

What is claimed and desired to be protected by Letters Patent:

1. A system comprising:
   a lead having a distal portion configured to be adjacent to a stimulation site within a patient and a proximal portion configured to be formed into at least a complete loop;
   a stimulator coupled to a proximal end of said lead;

a first suture sleeve configured to secure said lead to a first securing site to maintain said distal portion of said lead adjacent to said stimulation site;

a second suture sleeve configured to be located along said loop and secure said lead at a second securing site, wherein at least the second suture sleeve comprises at least one slit disposed in a body of the second suture sleeve, wherein the at least one slit is bound on four sides by a first pair of surfaces of the body that oppose and face each other and a second pair of surfaces of the body that oppose and face each other and that connect the first pair of surfaces, and wherein the at least one slit extends from an exterior of the second suture sleeve to a lumen of the second suture sleeve within which a portion of the lead is disposed; and adhesive disposed in the at least one slit and in the lumen of the second suture sleeve and in contact with the portion of the lead disposed in the second suture sleeve.

2. The system of claim 1, wherein said stimulation site comprises at least one or more of a greater occipital nerve, a lesser occipital nerve, and a greater auricular nerve.

3. The system of claim 1, wherein said one or more securing sites comprise at least one or more of a fascia and a bone.

4. The system of claim 1, wherein the first suture sleeve comprises:
a lumen configured to facilitate passage therethrough of said lead;
at least one slit disposed in a body of the first suture sleeve;
at least one groove disposed on the body of the first suture sleeve;
at least one wing member extending away from the body of the first suture sleeve, and
one or more holes disposed in the at least one wing member for suturing the first suture sleeve to the first securing site.

5. The system of claim 1, further comprising:
another lead having a distal portion configured to be adjacent to another stimulation site within said patient, a proximal portion configured to be formed into at least a complete loop, and a distal end configured to be coupled to said stimulator;
a third suture sleeve configured to secure said another lead to a third securing site to maintain said distal portion of said another lead adjacent to said another stimulation site; and
a fourth suture sleeve configured to be located along said loop of said another lead and secure said another lead at a fourth securing site.

6. The system of claim 5, wherein:
said loop of said lead is configured to be located entirely to the right of a midline of said patient; and
said loop of said another lead is configured to be located entirely to the left of said midline of said patient.

7. The system of claim 1, wherein said lead has at least one electrode disposed thereon, and wherein said stimulator is configured to apply an electrical stimulation current to said stimulation site via said at least one electrode.

8. The system of claim 7, wherein said electrical stimulation current is configured to treat a headache.

9. The system of claim 1, further comprising at least one catheter coupled to the stimulator.

10. The system of claim 1, wherein the at least one slit is linear.

11. The system of claim 1, wherein the second suture sleeve comprises
a first groove disposed on the body of the second suture sleeve;
a first wing member extending away from the body of the second suture sleeve, and
a first hole disposed in the first wing member for suturing the second suture sleeve to the second securing site.

12. The system of claim 11, wherein the first wing member intersects with the first groove.

13. The system of claim 12, wherein the first hole disposed in the first wing member is in an in-line alignment with the first groove.

14. The system of claim 13, wherein the second suture sleeve further comprises
a second groove disposed on the body of the second suture sleeve;
a second wing member extending away from the body of the second suture sleeve, and
a second hole disposed in the second wing member for suturing the second suture sleeve to the second securing site, wherein the second wing member intersects with the second groove and the second hole disposed in the second wing member is in an in-line alignment with the second groove.

15. The system of claim 14, wherein the first and second wing members extend away from the body of the second suture sleeve in opposite directions and are disposed in a staggered arrangement along a length of the second suture sleeve.

16. The system of claim 11, wherein the first groove intersects with a one of the at least one slit.

* * * * *